(12) United States Patent
Portugal et al.

(10) Patent No.: US 7,888,488 B2
(45) Date of Patent: Feb. 15, 2011

(54) **COMPOSITIONS AND METHODS FOR DIFFERENTIATING AMONG *SHIGELLA* SPECIES AND *SHIGELLA* FROM *E. COLI* SPECIES**

(76) Inventors: Franklin H. Portugal, 9105 Fall River La., Potomac, MD (US) 20854; Rita R. Colwell, 5010 River Hill Rd., Bethesda, MD (US) 20816; Anwarul Huq, 4306 Regalwood Terr., Burtonsville, MD (US) 20866; Afzal Chowdhury, 8881 Goose Landing Cir., Columbia, MD (US) 21045

( * ) Notice: Subject to any disclaimer, the term of this patent is extended or adjusted under 35 U.S.C. 154(b) by 2107 days.

(21) Appl. No.: 09/027,439

(22) Filed: Feb. 20, 1998

(65) Prior Publication Data

US 2002/0006611 A1 Jan. 17, 2002

Related U.S. Application Data

(60) Provisional application No. 60/038,117, filed on Feb. 20, 1997.

(51) Int. Cl.
C07H 21/02 (2006.01)
C07H 21/04 (2006.01)
(52) U.S. Cl. ..................... 536/23.1; 536/24.3
(58) Field of Classification Search .............. 435/6, 435/91.1, 91.2; 536/23.1, 24.3
See application file for complete search history.

(56) References Cited

U.S. PATENT DOCUMENTS

| | | | |
|---|---|---|---|
| 4,724,205 A | 2/1988 | Karlsson et al. | 435/38 |
| 4,992,364 A | 2/1991 | Sansonetti et al. | 435/6 |
| 5,041,372 A | 8/1991 | Lampel et al. | 435/6 |
| 5,084,565 A | 1/1992 | Parodos et al. | 536/27 |
| 5,089,386 A | 2/1992 | Stackebrandt et al. | 435/6 |
| 5,189,151 A | 2/1993 | Baudry et al. | 536/24 |
| 5,217,862 A | 6/1993 | Barns et al. | 435/6 |
| 5,374,718 A * | 12/1994 | Hammond | |
| 5,376,528 A | 12/1994 | King et al. | 435/6 |
| 5,474,796 A * | 12/1995 | Brennan | 427/2.13 |
| 5,541,308 A * | 7/1996 | Hogan | 536/23.1 |
| 5,601,984 A | 2/1997 | Kohne | 435/6 |
| 5,714,321 A * | 2/1998 | Hogan | 435/6 |

OTHER PUBLICATIONS

Accession No. X80724, Mar. 1996.*
Accession No. X80723, Mar. 1996.*
Accession No. X80726, Mar. 1996.*
Dyson, NJ. Essential Molecular Biology vol. II: A Practical Approach, chapter 5, pp. 111-156, Brown, T.A. ed. Oxford University Press, Oxford, 1992.*
Accession No. A14565, Genbank, Sep. 29, 1994.*
Accession No. J01695, Genbank, Apr. 15, 1994.*
Accession No. U18997, genbank, Dec. 1994.*
Accession No. X80679, Feb. 20, 1996.*
Accession No. X80729, Feb. 20, 2996.*
Accession No. X80678, Feb. 20, 1996.*
Accession No. X80730, Feb. 20, 1996.*
Ahern, The Scientist, vol. 9, pp. 1-5.*
Anderson, Gene Probes 2: Hybridization strategy, Oxford University Press, New York, 1995; Hames and Higgins eds.*
Genbank accession No. X96964, NCBI; Apr. 1996; alignment provided.*
Genbank accession No. X80726, NCBI; Mar. 1996; alignment provided.*
Cilia et al.; Mol. Biol. Evol. vol. 13, pp. 451-461; Feb. 20, 1996.*
Genbank accession No. A14565; NCBI, Sep. 1994, alignment provided.*
Dyson, NJ. Essential Molecular Biology, vol. II: A Practical Approach, chapter 5, pp. 1111-1156, Brown, T.A. ed. Oxford University Press, Oxford 1992.*
Cilia et al., "Sequence Heterogeneities Among 16S Ribosomal RNA Sequences, and Their Effect on Phylogenetic Analyses at the Species Level", Mol. Biol. Evol. 13(3):451-461, Feb. 1996.
Faruque et al., "Differentiation of *Shigella flexneri* Strains by rRNA Gene Restriction Patterns", J. Clinical Microbiology, Nov. 1992, p. 2996-2999.
Nastasi et al., "Molecular Analysis of Strains of *Shigella boydii* Isolated in Northern and Southern Italy", Res. Microbiol. 1990, 141, 1163-1172.
Search to *Shigella* detection, Nov. 20, 1996.
Search to "Ribosomal RNA" Nov. 18, 1996.
Search to "*Shigella*" prior to Feb. 20, 1997.
ECL 3' Oligolabeling and Detection System Instruction Booklet, pp. 6-9 and 30-31. Prior to Feb. 20, 1997.
Invitrogen Catalog page for pCR™II. Prior to Feb. 20, 1997.
GenBank Database printout, 16s rRNA, Aug. 13, 1996.
GenBank S. sonnei 16s rRNA gene. May 9, 1996.
GenBank S. sonnei 16s rRNA gene. Mar. 29, 1996.
GenBank S. boydii 16s rRNA gene. May 9, 1996.
GenBank S. dysenteriae 16s rRNA gene. May 9, 1996.
GenBank S. dysenteriae 16s rRNA gene. Mar. 29, 1996.
GenBank S. flexneri 16s rRNA gene. May 9, 1996.
GenBank S. flexneri 16s rRNA gene. Mar. 29, 1996.

* cited by examiner

Primary Examiner—Jehanne S Sitton

(57) ABSTRACT

The present invention relates to detecting and distinguishing among bacteria that belong to the species *Shigella*, including *Shigella boydii*, *Shigella dysenteriae*, *Shigella flexneri*, and *Shigella sonnei*; and detecting and distinguishing *Shigella* bacteria from *Escherichia coli*. In particular, the invention includes provision of species-identifying and genus-identifying nucleotides of 16s rRNA or 16s rDNA from the above named species. Nucleic acid probe molecules capable of differentiating among these species and genera by hybridization, along with methods for their use for specific detection in clinical samples, food samples, environmental samples, and the like are also provided.

7 Claims, No Drawings

US 7,888,488 B2

COMPOSITIONS AND METHODS FOR DIFFERENTIATING AMONG *SHIGELLA* SPECIES AND *SHIGELLA* FROM *E. COLI* SPECIES

The present application claims priority to U.S. provisional application Ser. No. 60/038,117, filed Feb. 20, 1997.

FIELD OF THE INVENTION

The present invention relates to distinguishing particular species of bacteria belonging to the genus *Shigella* and discriminating *Shigella* from *E. coli*. More specifically, an aspect of the invention provides species-specific and genus-specific identifying nucleotides for the design of nucleic acid probes for the detection and identification of *Shigella* species and for the discrimination between *Shigella* and *E. coli*, compositions thereof, and methods for their use.

BACKGROUND OF THE INVENTION

Shigellosis, also known as bacillary dysentery, is caused by several bacteria of the genus *Shigella*. Symptoms include diarrhea, abdominal pain, vomiting and fever. Generally, foodborne shigellosis involves a short incubation time, but symptoms can persist for up to 14 days. As few as 10 to 100 organisms have been shown to cause illness and secondary infections occur frequently. In the United States, *Shigella* accounts for up to 25% of the total cases of intestinal disease. The actual number of cases is estimated to be currently about 350,000. The proliferation of childcare facilities is playing an increasing important role in disease outbreaks.

*Shigella* infection is a serious public health problem in the United States and, as such, physicians are required to report cases to the Centers for Disease Control and Prevention. Further, recent changes in government regulations will make it incumbent upon the food industry to report enteric bacterial contamination of food. Public Health Laboratories, operated by the States, often must test specimens provided by physicians in order to identify the specific species of *Shigella* causing infection.

*Shigella* is an invasive pathogen that can be recovered from the bloody stool of an infected host. Invasive pathogens colonize the host's tissues as opposed to growing on tissue surfaces. Therefore, infections are also associated with mucosal ulceration, rectal bleeding, and drastic dehydration; fatality may be as high as 10-15% with some strains. Reiter's disease, reactive arthritis, and hemolytic uremic syndrome are possible sequelae that have been reported in the aftermath of shigellosis. Infants, the elderly, and the infirm are susceptible to the severest symptoms of disease, but all humans are susceptible to some degree. Shigellosis is a very common malady suffered by individuals with AIDS and AIDS-related complex, as well as non-AIDS homosexual men.

Transmission is frequently by ingestion of contaminated food or water. The organisms survive the gastric milieu and make it to the large intestine where the bacteria attach to specific host cells via invasins and then invade the epithelial cells lining the large intestines. Additional cell death is produced by elaboration of shiga toxins. Shiga toxin is a cytotoxin (or enterotoxin) that destroys epithelial cells lining the lumen of the large intestine; this causes bloody diarrhea characteristic of *Shigella* infection. Plasmid-mediated invasins determine the virulence of the particular strain of *Shigella*. Symptoms develop after an incubation period of 24 to 48 hours and include fever, abdominal pain and diarrhea.

The genus *Shigella* is a member of the family of Enterobacteriaceae and is thus related to *Escherichia coli*. Their DNA relatedness is very high, they are often difficult to differentiate biochemically, and they cross-react serologically. However, they have remained separate species for clinical reasons. Enterohemorrhagic *E. coli* (EHEC) is a defined subset of toxin-producing *Shigella* and at least one serotype (0157:H7) of EHEC can cause hemorrhagic colitis and hemolytic uremic syndrome, a potentially fatal complication.

The four species in the *Shigella* genus are sometimes referred to by a letter designation based on their serological antigen:

Serotype A—*S. dysenteriae*
Serotype B—*S. flexneri*
Serotype C—*S. boydii*
Serotype D—*S. sonnei*

Serotype D is the causative agent of most cases of *Shigella*-related diarrhea. Although all *Shigella* species have been implicated in foodborne outbreaks at some time, *S. sonnei* is thought to be the leading cause of shigellosis from food. The other species are more closely associated with contaminated water. One in particular, *S. flexneri*, is now thought to be in large part sexually-transmitted.

Current laboratory methods for detecting *Shigella* depend on growing the organism from a stool or food sample on culture plates and distinguishing it from other organisms on the basis of growth characteristics and biochemical tests. However, conventional testing currently is difficult. Growth on MacConkey agar may yield colonies of *Shigella* and *E. coli* that are both colorless, lactose negative, and about 2-3 mm in diameter. Growth of both organisms on sheep blood agar yields colonies that are alike, having a smooth appearance and 2-3 mm in diameter. Tube testing is widely used in reference and public health laboratories. Unfortunately, the media and tests used are not well standardized, and few laboratories use exactly the same procedures. Some 47 biochemical reactions are numerated to help distinguish between named species, biogroups, and enteric groups of the family Enterobacteriaceae. These tests are labor-intensive and costly. A genetic probe to a virulence plasmid has been developed by FDA and is currently under field test. Blood serology can also be used to distinguish one species from another. Although the Centers for Disease Control require distinguishing among the four major species of *Shigella* in its reporting statistics, it is difficult to do so.

Distinguishing between *Shigella* and *E. coli* is important for treating the infection. Diarrhea and other symptoms caused by infection with *Shigella* is one form of bacterial-caused intestinal inflammation in which antibiotic therapy has been clearly shown to reduce the duration and severity of symptoms and to shorten the period of fecal excretion of the organism. Thus, antibiotic therapy is generally recommended for all patients with *Shigella* diarrhea, except those with mild, self-limited disease. The recommended antibiotic is trimethoprim-sulfamethoxazole. Ampicillin-resistant strains are becoming a problem. There is no acquired immunity to infection and no vaccine exists. In contrast, there is no evidence that use of antimicrobial agents to treat *E. coli* 0157:H7 disease changes the course of the disease or is beneficial in any way. Distinguishing among the species of *Shigella* is not only important for proper reporting to the centers for Disease Control, but also for determining differing susceptibilities to antibiotics.

U.S. Pat. No. 4,724,205 relates to a composition for therapeutic treatment or diagnosis of the toxin associated with *Shigella dysenteriae*. U.S. Pat. No. 4,992,364 to Sansonetti et al. relates to a probe for DNA and a process for detection of *Shigella* and enteroinvasive strains of *E. coli*. The probe reportedly contained a nucleic acid sequence originating from the 140 mDa virulence plasmid of the M 90 T strain of *Shigella flexneri*, which permitted the in vitro diagnosis of syndromes of dysentery or diarrhea of the shigellosis type. The probe, however, could not distinguish either between *E. coli* and *Shigella* or between the different species of *Shigella*. A similar strategy was apparently employed by Lampel and Jagow (U.S. Pat. No. 5,041,372), but had the advantage of using synthetic oligodeoxyribonucleotides, which are more stable and easier and cheaper to make then the fragments prepared with restriction enzymes from the virulence plasmid. U.S. Pat. No. 5,084,565 to Parodos et al. relates to nucleic acid probes capable of specifically hybridizing to rRNA of *E. coli* and *Shigella* species and not to rRNA of non-*E. coli/Shigella* species. The hybridization assay could not distinguish either between *Shigella* and *E. coli* or between the different genera of *Shigella*. Faruque et al. (*J. Clin. Microbiol.* 30(11):2996, 1992) reports differentiation of *Shigella flexneri* strains by rRNA gene restriction patterns. Nastasi et al. (*Res. Microbiol.* 141:1163, 1990) reports the molecular analysis of strains of *Shigella boydii* isolated in northern and southern Italy.

Present detection methods using nucleic acid identity are not able to distinguish *Shigella* species from *E. coli* or *Shigella* species from each other. Therefore, known procedures are not completely satisfactory, and the present inventors provide herein compositions and methods for distinguishing *Shigella* from *E. coli* and species of *Shigella* from each other.

SUMMARY OF THE INVENTION

The present invention seeks to overcome these and other drawbacks inherent in the prior art by providing species-specific and genus-specific and, therefore, species-identifying and genus-identifying, nucleotides of 16s rRNA (and therefore, also of 16s rDNA) from *Shigella flexneri, Shigella sonnei, Shigella boydii*, and *Shigella dysenteriae*. The species-specific nucleotides provided herein allow detection and identification of *Shigella* species present in a test sample. "Species-specific," as used herein, means that detection of an identifying nucleotide determines presence of that species, while lack of detection of a particular identifying nucleotide does not necessarily mean absence of that species. Further, genus-specific nucleotides are provided that distinguish *Shigella* and *E. coli*. "Genus-specific," as used herein, means that detection of an identifying nucleotide determines presence of that genus, while lack of detection of a particular identifying nucleotide does not necessarily mean absence of that genus.

By "identifying or distinguishing nucleotide" is meant a nucleotide that differs in kind or in its presence or absence as compared to an *E. coli*-equivalent position. Nucleotide, as used herein, is meant in include the corresponding nucleoside without phosphate attached, or the corresponding free base. One of skill in the art realizes that the specificity relies in the base, not the sugar or phosphate and that the bases will usually be present in the form of a nucleotide for purposes of the present invention. Although the sequences presented herein including in the sequence listing and tables depict the DNA sequence having a thymine rather than a uracil as would be present in RNA, one of skill in the art would realize in light of the present disclosure that detection of a uracil base in RNA would be equivalent to detection of a T base in DNA and such equivalents are intended to be included in the scope of the claims. "Identifying or distinguishing nucleotide," as used herein, is meant to include a combination of one or more nucleotides, the combination being identifying of a species or of a genus.

While identifying nucleotides and identifying combinations of nucleotides are specifically provided herein from sense strand information, one of skill in the art would realize, in light of the present disclosure, that a nucleotide on a complementary strand of nucleic acid complementary to an identifying nucleotide is also identifying.

Accordingly, the present invention provides an identifying nucleotide or identifying combination of nucleotides of 16s ribosomal RNA or 16s ribosomal DNA as set forth in Table 2 present in a *Shigella* species and not present in *E. coli*. The reference numbering system of Table 2 is the rDNA sequence corresponding to the rRNA sequence of *E. coli* 16s rRNA strain 7 as provided in GenBank as ECORRD, and as provided as SEQ ID NO:7. The sequences of 16s rRNA or rDNA of *Shigella* species regions are aligned to maximally match the *E. coli* sequence. To maximize alignment, adjustments are made in the *Shigella* sequence, not the *E. coli* sequence. For example, as herein described, an insertion of a nucleotide into the *Shigella* sequence as compared to the *E. coli* sequence is designated herein as a "p" nucleotide. A deletion is designated as an "X" nucleotide. "*E. coli*-equivalent position," as used herein, means that such an alignment of *Shigella* sequences has been carried out and an *E. coli* equivalent number has been assigned to a *Shigella* nucleotide position.

A further aspect of the present invention is an identifying nucleotide or identifying combination of nucleotides of 16s ribosomal RNA or 16s ribosomal DNA as set forth in Table 2 present in *E. coli* and not present in a *Shigella* species.

Another aspect of the invention is an identifying nucleotide or identifying combination of nucleotides of 16s ribosomal RNA or 16s ribosomal DNA as set forth in Table 2 present in one species selected from the group consisting of *Shigella sonnei, Shigella flexneri, Shigella boydii*, and *Shigella dysenteriae*, and not present in the other species of *Shigella* and not present in *E. coli*.

Purified nucleic acid molecules used as probe molecules and capable of hybridizing to nucleic acid sequences having an identifying nucleotide are part of the present invention. Accordingly, a purified nucleic acid molecule capable of hybridizing to a 16s rRNA region or a 16s rDNA region having a genus-specific nucleotide of *Shigella* and not to an equivalent 16s rRNA region or 16s rDNA region of *E. coli*, or a nucleic acid molecule complementary to said molecule, the molecule thereby capable of distinguishing *Shigella* from *E. coli* is a further aspect of the present invention. One of skill in the art would realize that a hybridizing molecule preferably would be designed to have sequence complementarity to a region of interest. Detection of an identifying nucleotide of a complementary strand sequence is intended to fall within the spirit and scope of the present invention. An assay kit for distinguishing *Shigella* from *E. coli* comprising a purified nucleic acid molecule as provided herein packaged in at least one container is a further aspect of the invention.

A further aspect of the invention is a purified nucleic acid molecule capable of hybridizing to a 16s rRNA region or a 16s rDNA region having a genus-specific nucleotide of *E. coli* and not to an equivalent 16s rRNA region or 16s rDNA region of a *Shigella* species, or a nucleic acid molecule complementary to said molecule, the molecule thereby capable of distinguishing *E. coli* from *Shigella*. An assay kit for distinguishing *E. coli* from *Shigella* comprising a purified nucleic acid molecule as provided herein packaged in at least one container is a further aspect of the present invention.

A set of probes may be used for determination of a genus or species. A first probe may eliminate certain species, while further hybridization with a second probe may then provide a definitive determination of genus or species. Accordingly, a first and a second purified nucleic acid molecule combination, the first capable of hybridizing to a first 16s rRNA region or 16s rDNA region as set forth in Table 2, the second capable of hybridizing to a second 16s rRNA region or 16s rDNA region as set forth in Table 2, the combination of molecules thereby capable of distinguishing *E. coli*, or a *Shigella* species, or a nucleic acid molecule combination complementary to said first and second molecules is an aspect of the invention.

In particular, a combination of molecules for hybridizing to rRNA or rDNA of *Shigella flexneri* and not to rRNA or rDNA of *E. coli*, *Shigella sonnei*, *Shigella boydii*, or *Shigella dysenteriae*, or a set of nucleic acid molecules complementary to said combination is a further aspect of the present invention. A particular combination of nucleic acid molecules is wherein the first molecule hybridizes to a *Shigella flexneri* region containing a G nucleotide at position 79, and the second molecule hybridizes to *Shigella flexneri* region containing a G nucleotide at position 89 or to *Shigella flexneri* region containing a C nucleotide at position 92p. An assay kit for identifying *S. flexneri* as distinct from other *Shigella* species comprising a combination of nucleic acid molecules as herein described in at least one container is an aspect of the invention.

A purified nucleic acid molecule capable of hybridizing to 16s rRNA region or 16s rDNA region of *Shigella sonnei* and not to 16s rRNA region or 16s rDNA region of *E. coli*, *Shigella flexneri*, *Shigella boydii*, or *Shigella dysenteriae*, or a nucleic acid molecule complementary to said molecule is a further aspect of the present invention. In particular, the molecule may have a nucleotide sequence of SEQ ID NO: 20; or may have a nucleotide sequence that detects a C at position 964, or the absence of a base at *E. coli*-equivalent position 978. An assay kit for identifying *S. sonnei* as distinct from other *Shigella* species comprising a nucleic acid molecule as described herein packaged in at least one container is a further embodiment of the invention.

Another embodiment of the present invention is a nucleic acid molecule capable of hybridizing to 16s rRNA region or 16s rDNA region of *Shigella boydii* and not to 16s rRNA region or 16s rDNA region of *E. coli*, *Shigella flexneri*, *Shigella sonnei*, or *Shigella dysenteriae*, or a nucleic acid molecule complementary to said molecule. In particular, the molecule may have a nucleotide sequence that detects a C at position 92. An assay kit for identifying *S. boydii* as distinct from other *Shigella* species comprising a nucleic acid molecule as described herein packaged in at least one container is another aspect of the invention.

A purified nucleic acid molecule capable of hybridizing to 16s rRNA region or 16s rDNA region of *Shigella dysenteriae* and not to 16s rRNA region or 16s rDNA region of *E. coli*, *Shigella flexneri*, *Shigella sonnei*, or *Shigella boydii*, or a nucleic acid molecule complementary to said molecule is another embodiment of the present invention. In particular, the molecule may have a nucleotide sequence that detects an A at position 76. An assay kit for identifying *S. dysenteriae* as distinct from other *Shigella* species comprising a nucleic acid molecule as herein described packaged in at least one container is an aspect of the invention.

Purified nucleic acid molecules having a nucleotide sequence of the 16s rRNA or rDNA of the *Shigella* species provided herein are also an aspect of the present invention. Accordingly, a purified nucleic acid molecule having a nucleotide sequence as set forth in SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 14, SEQ ID NO: 16, SEQ ID NO: 17, SEQ ID NO: 18, SEQ ID NO: 19, SEQ ID NO: 20, or SEQ ID NO: 21 or a nucleic acid complementary to said purified molecule is a further aspect of the present invention.

A method for testing an unknown sample suspected of having *E. coli* or *Shigella* species presence comprising demonstrating an identifying nucleotide or identifying combination of nucleotides of 16s rRNA or 16s rDNA as set forth in Table 2 within the sample, wherein the demonstration of an identifying nucleotide or identifying combination of nucleotides establishes presence or absence of *E. coli* or *Shigella* in the sample is a further embodiment of the present invention. The unknown sample may be a clinical sample for diagnosis, a food sample, or an environmental sample, for example. The method could be any of a number of methods of looking at particular nucleic acid sequences, for example, direct sequencing, dot-blot hybridization, solution hybridization, Southern or Northern blotting, PCR amplification of a target region followed by any of above methods and as described further herein. Preferably, the demonstrating is by a method selected from the group consisting of direct sequencing, dot blot hybridization, solution hybridization, Northern blotting, and Southern blotting of the unknown sample. Further methods may be known to one of skill in the art in light of the present disclosure.

In particular, the unknown sample may be suspected of containing *E. coli* and the identifying nucleotide is a T at position 88p; the unknown sample may be suspected of containing *Shigella sonnei* and the identifying nucleotide is a C at position 964, or a deletion at position 978; the unknown sample may be suspected of containing *Shigella dysenteriae* and the identifying nucleotide is an A at position 76; the unknown sample may be suspected of containing *Shigella boydii* and the identifying nucleotide is a C at position 92; or the unknown sample is suspected of containing *Shigella flexneri* and the identifying nucleotide is a G nucleotide at position 79 in combination with a G at position 89 or a C at position 92p.

A particular advantage of the present invention is the heretofore nonexistent ability to distinguish and identify *Shigella* versus *E. coli* using nucleic acid probes and distinguish and identify the four *Shigella* species cited herein using molecular identification of species-specific nucleotides or genus-specific nucleotides. Identification of the species- and genus-specific nucleotides, and thereby, identification of the organism, can be now facilitated with increased sensitivity, i.e., the ability to detect these bacteria in a given sample more frequently than currently available methods, with reductions in assay cost due to less expensive reagents and reduced labor, with accurate identification, and with faster results because the test does not require the isolation of bacteria from a cultured sample prior to testing.

Following long-standing patent law convention, the terms "a" and "an" mean "one or more" when used in this application, including the claims.

DETAILED DESCRIPTION OF THE PREFERRED EMBODIMENTS

The present invention relates to detecting and distinguishing among bacteria that belong to the species *Shigella*, including *Shigella* boydii, *Shigella* dysenteriae, *Shigella flexneri*, and *Shigella sonnei*; and detecting and distinguishing *Shigella* bacteria from *Escherichia coli*. In particular, the invention includes provision of species-identifying and genus-identifying nucleotides of 16s rRNA or 16s rDNA from the above named species. Nucleic acid probes capable of differentiating among these species and genera by hybridization, along with methods for their use for specific detection in clinical samples, food samples, environmental samples, and the like are also provided.

As used herein, the term "nucleic acid molecule" may refer to a DNA or RNA molecule which has been isolated free of total genomic nucleic acid. Therefore, a "purified" nucleic acid molecule, as used herein, refers to a nucleic acid molecule that contains ribosomal RNA or a ribosomal DNA gene or fragment thereof, yet is isolated away from, or purified free from, total cellular RNA or total cellular DNA. "Purified" nucleic acid molecules also refer to those made synthetically. Included within the term "nucleic acid molecule" are nucleic acid segments and smaller fragments of such segments.

The term "rRNA or rDNA" is used for simplicity to refer to 16s ribosomal ribonucleic acid or 16s ribosomal deoxyribonucleic acid. Ribosomal RNA is usually single-stranded and will hybridize to complementary RNA or DNA fragments, or if self-complementarity exists, will hybridize to itself to form double-stranded regions. An oligonucleotide probe may also hybridize to a complementary region of RNA. Ribosomal DNA, as used herein, refers to the gene that encodes rRNA; rDNA is usually double-stranded, can be melted to a single-stranded form, and will hybridize to complementary RNA or DNA fragments. An oligonucleotide probe will also hybridize to a complementary region of double-stranded DNA to form a triple helix region.

Table 1 lists the identity of sequences of the present disclosure having sequence identifiers.

TABLE 1

Identification of Sequences Having Sequence Identifiers

| SEQ ID NO: | IDENTITY |
|---|---|
| 1 | nucleotide sequence of a forward primer for amplifying 16s rDNA gene by PCR |
| 2 | nucleotide sequence of a reverse primer for amplifying 16s rDNA gene by PCR |
| 3 | nucleotide sequence of 16s rDNA of *Shigella flexneri* provided by the present disclosure |
| 4 | nucleotide sequence of 16s rDNA of *Shigella sonnei* provided by the present disclosure |
| 5 | nucleotide sequence of 16s rDNA of *Shigella dysenteriae* provided by the present disclosure |
| 6 | nucleotide sequence of 16s rDNA of *Shigella boydii* provided by the present disclosure |
| 7 | nucleotide sequence of 16s rDNA of *E. coli* strain 7 having Genbank Identifier ECORRD from Genbank |
| 8 | nucleotide sequence of region 71-00 of *E. coli* 16s rDNA strain 7 |
| 9 | nucleotide sequence of region 71-00 of *S. flexneri* 16s rDNA provided by the present disclosure |
| 10 | nucleotide sequence of region 71-100 of *S. sonnei* 16s rDNA provided by the present disclosure |
| 11 | nucleotide sequence of region 71-100 of *S. dysenteriae* 16s rDNA provided by the present disclosure |
| 12 | nucleotide sequence of region 71-100 of *S. boydii* 16s rDNA provided by the present disclosure |
| 13 | nucleotide sequence of region 961-991 of *E. coli* 16s rDNA strain 7 |
| 14 | nucleotide sequence of region 961-991 of *S. sonnei* 16s rDNA provided by the present disclosure |
| 15 | nucleotide sequence of region 1001-1040 of *E. coli* 16s rDNA strain 7 |
| 16 | nucleotide sequence of region 1001-1040 of *S. sonnei* 16s rDNA provided by the present disclosure |
| 17 | nucleotide sequence of region 1001-1040 of *S. dysenteriae* 16s rDNA provided by the present disclosure |

TABLE 1-continued

Identification of Sequences Having Sequence Identifiers

| SEQ ID NO: | IDENTITY |
|---|---|
| 18 | nucleotide sequence of 80-100 of *S. boydii* provided by the present disclosure |
| 19 | nucleotide sequence of 76-94 of *S. dysenteriae* provided by the present disclosure |
| 20 | nucleotide sequence of 961-980 of *S. sonnei* provided by the present disclosure |
| 21 | a composite nucleotide sequence of 79-98 for *E. coli* |
| 22 | a portion of SEQ ID NO: 20 prior to X as shown in Table 3 |

A purified nucleic acid molecule of a *Shigella* species of the present invention may have a nucleotide sequence set forth as SEQ ID NO:3, SEQ ID NO:4, SEQ ID NO:5, or SEQ ID NO:6, or fragments of said sequences. Unique species-specific and genus-specific DNA probes are provided as SEQ ID NOS: 9-12, 14, 16-21, or fragments thereof. The probes are complementary to areas of rRNA or rDNA having species-specific nucleotides or genus-specific nucleotides. Probe molecules of the present invention are provided for detecting and discriminating in a test sample the presence of rRNA or rDNA molecules of *Shigella* species and *E. coli*.

In certain aspects, the invention concerns isolated DNA segments that include within their sequence a nucleic acid sequence essentially as set forth in SEQ ID NO:3-21. The term "essentially as set forth" means that the nucleic acid sequence substantially corresponds to a portion of SEQ ID NO:3-21, and has few nucleotides that are not identical, or functionally equivalent, to the nucleotides of said sequences. The term "functionally equivalent nucleotide" is used herein to refer to nucleotides capable of hydrogen bonding to a complementary nucleotide in a similar manner and degree to that of a natural nucleotide. A thymine base may be replaced by a uracil base, for example. A "functionally equivalent nucleotide" includes, but is not limited to, derivatized nucleotides such as methylated nucleotides; nucleotide analogs such as xanthine, hypoxanthine, inosine, and the like. One of skill in the art, in light of the present disclosure, would be able to alter one or more nucleotides of a probe molecule as described herein and maintain ability to detect identifying nucleotides.

Nucleic acid molecules may include additional residues, such as additional 5' or 3' nucleotides, and yet still be essentially as set forth in one of the sequences disclosed herein, so long as the sequence meets the criteria set forth herein, including the maintenance of hybridizing activity. End-capped oligonucleotides may be incorporated into the nucleic acid molecules of the present invention. End-capped probes contain chemical moieties that block the 3' and/or 5' terminal hydroxyl groups of the oligonucleotide chains providing stability since capped probes are no longer susceptible to degradation by exonucleases known to degrade oligonucleotides. Indicator molecules, such as fluorophores, radioactive labels, peptides, or the like may be attached to nucleic acid molecules of the present invention at the 3' end, the 5' end, or at other locations on the molecule, and still fall within the scope of the claimed invention.

The present invention includes a purified nucleic acid molecule complementary, or essentially complementary, to the nucleic acid molecule having the sequence set forth in SEQ ID NO:3-21 or a fragment thereof. Nucleic acid sequences which are "complementary" are those that are capable of base-pairing according to the standard Watson-Crick complementarity rules. As used herein, the term "complementary sequences" means nucleic acid sequences which are substantially complementary or as defined as being capable of hybridizing to the nucleic acid segment of said sequences under relatively stringent conditions. Complementary nucleotide sequences are useful for detection and purification of hybridizing nucleic acid molecules.

For general reviews of synthesis of DNA, RNA, and their analogues, see *Oligonucleotides and Analogues*, F. Eckstein, Ed., 1991, IRL Press, New York; *Oligonucleotide Synthesis*, M. J. Gait, Ed., 1984, IRL Press Oxford, England; Caracciolo et al. (1989); *Bioconjugate Chemistry*, Goodchild, J. (1990); or for phosphonate synthesis, Matteucci, M D. et al., *Nucleic Acids Res*. 14:5399 (1986) (the references are incorporated by reference herein).

In general, there are three commonly used solid phase-based approaches to the synthesis of oligonucleotides containing conventional 5'-3' linkages. These are the phosphoramidite method, the phosphonate method, and the triester method.

A brief description of a current method used commercially to synthesize oligomeric DNA is as follows: Oligomers up to ca. 100 residues in length are prepared on a commercial synthesizer, eg., Applied Biosystems Inc. (ABI) model 392, that uses phosphoramidite chemistry. DNA is synthesized from the 3' to the 5' direction through the sequential addition of highly reactive phosphorous(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add a further residue until the desired DNA polymer is synthesized. The full length polymer is released from the solid support, with concomitant removal of remaining protective groups, by exposure to base. A common protocol uses saturated ethanolic ammonia.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete. The phosphonates can also be converted to phosphoramidate derivatives by reaction with a primary or secondary amine in the presence of carbon tetrachloride.

In the triester synthesis, a protected phosphodiester nucleotide is condensed with the free hydroxyl of a growing nucleotide chain derivatized to a solid support in the presence of coupling agent. The reaction yields a protected phosphate linkage which may be treated with an oximate solution to form unprotected oligonucleotide.

To indicate the three approaches generically, the incoming nucleotide is regarded as having an "activated" phosphite/phosphate group. In addition to employing commonly used solid phase synthesis techniques, oligonucleotides may also be synthesized using solution phase methods such as diester synthesis. The methods are workable, but in general, less efficient for oligonucleotides of any substantial length.

Preferred oligonucleotides resistant to in vivo hydrolysis may contain a phosphorothioate substitution at each base (*J.* *Org. Chem.*, 55:4693-4699, (1990) and Agrawal, (1990)). Oligodeoxynucleotides or their phosphorothioate analogues may be synthesized using an Applied Biosystem 380B DNA synthesizer (Applied Biosystems, Inc., Foster City, Calif.).

Ribonucleotides may be synthesized with protecting groups on the free ribose oxygen, i.e., a O'-alkyl group, for example. The alkyl is preferably a methyl, although ethyl or propyl may be used also.

Oligonucleotides may also be synthesized by application of nucleic acid reproduction technology, such as the PCR technology of U.S. Pat. No. 4,683,202 (herein incorporated by reference).

Hybridization is a process where, under predetermined reaction conditions, partially or completely complementary nucleic acids are allowed to come together in an antiparallel fashion to form a double-stranded or triple-stranded nucleic acid with specific and stable hydrogen bonds.

Oligonucleotide probes are useful in hybridization embodiments such as Southern or Northern blotting, or dot blot hybridization, for detection of the presence in a test sample of species-specific or genus-specific nucleotides of the present invention. The total size of fragment, as well as the size of the complementary regions, will depend on the intended use or application of the particular nucleic acid segment. Smaller fragments will generally find use in hybridization embodiments where the length of the complementary region may be varied, such as between about 10 and about 40 nucleotides. The use of a hybridization probe of about 10 nucleotides in length allows the formation of a duplex molecule that is both stable and selective. Molecules having complementary sequences over stretches greater than 10 bases in length are generally preferred to increase stability and selectivity of the hybrid, and thereby improve the quality and degree of specific hybrid molecules obtained. Nucleic acid probes having complementary regions of 15 to 25 nucleotides are most preferable.

Standard hybridization conditions is used to describe those conditions under which substantially complementary nucleic acid segments will form standard Watson-Crick base-pairing. A number of factor determine the specificity of binding or hybridization, such as pH, salt concentration, the presence of chaotropic agents (e.g. formamide and dimethyl sulfoxide), the length of the segments that are hybridizing, the base composition of the probe/target duplex, as well as by the level and geometry of mispairing between the nucleic acids. Stringency is also governed by reaction parameters such as the concentration and type of ionic species present in the hybridization solution, the types and concentrations of denaturing agents present, and/or the temperature of hybridization. Generally, as hybridization conditions become more stringent, longer probes are preferred if stable hybrids are to be formed.

As used herein, "probe" refers to synthetic or biologically produced nucleic acids that by design or selection contain specific deoxyribonucleotide or ribonucleotide sequences that allow them to hybridize under defined predetermined stringencies, specifically and preferentially to target nucleic acid sequences. A target nucleic acid sequence is one to which a particular probe is capable of preferentially hybridizing. As used herein, a target nucleic acid sequence contains a species-specific or genus-specific nucleotide.

Varying conditions of hybridization may be used to achieve varying degrees of selectivity of probe towards a target sequence. Stringent hybridization conditions may include hybridization to target nucleic acid sequences at 40°-65° C. for 14-16 h in a hybridization solution containing 0.9M NaCl, 0.12M Tris-HCl, pH 7.8, 6mM EDTA, 0.1M sodium phosphate buffer, 0.1% SDS, 0.1% polyvinylpyrrolidone, followed by three, 15-minute washes at 40°-65° C. to remove unbound probes in a solution containing 0.075M NaCl, 0.0075M Na Citrate, pH 7 and 0.1% SDS. Such selective conditions tolerate little, if any, mismatch between the probe and a test sample, and would be particularly suitable for detecting species-specific or genus-specific nucleotides.

The control of stringency can take place in the hybridization procedure. However, it is sometimes conveniently controlled in the post hybridization stringency washes. Stringency washes are usually performed at 3-5° C. below the Tm of the perfectly matched probe where discrimination from mismatched sequences is required. The Tm of an oligonucleotide can be calculated according to the rule:

$$Tm=(4\times\text{number of }G+C\text{ bases})+(2\times\text{number of }A+T\text{ bases}),$$

though it must be appreciated that this value is only an approximation (particularly for probes greater than 25 bases in length). Stringency can be controlled by alterations in the temperature or by changing the SSC concentration in the stringency wash.

Hybridization probes described herein are useful as reagents in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label. A wide variety of appropriate indicator means are known in the art, including fluorescent, radioactive, enzymatic or other ligands, such as avidin/biotin, which are capable of giving a detectable signal. In preferred embodiments, a fluorescent label or an enzyme tag, such as urease, alkaline phosphatase or peroxidase, may be used. In the case of enzyme tags, colorimetric indicator substrates are known which can be employed to provide a means visible to the human eye or spectrophotometrically, to identify specific hybridization with complementary nucleic acid-containing samples. Further, chemiluminescence, bioluminescence or radioactive indicators are recorded on sensitive film and the data converted to digitized information.

Further methods for detecting and identifying species-specific and genus-specific nucleotides of the present invention include direct sequencing of the region including said nucleotide, PCR amplification of said region followed by direct sequencing or hybridization or, if said nucleotide forms or destroys a restriction site, then restriction fragment length polymorphisms may be relied upon.

In another aspect, the present invention contemplates a diagnostic kit for screening a test sample for the presence of *Shigella* sp. or *E. coli*. Such a kit would contain a nucleic acid probe having specificity for a species-specific or genus-specific nucleotide provided by the present disclosure. Nucleic acid molecules, as probes, can be used in ELISA type assays. Nucleotides can be synthesized that carry peptides and these peptides could be identified with monoclonal or polyclonal antibodies. If the antibodies were linked to a signaling system such as an enzyme (horseradish peroxidase, for example), bioluminescence, chemiluminescence, radioactivity, fluorescence, or other known signal-generating systems, then the ELISA test could be developed. The kit may contain probes to be used as controls for the hybridization tests.

A test kit may include nucleic acid molecules having a nucleotide sequence of SEQ ID NOS: 9-12, 14, 16-21, or fragments thereof together with a negative control and a positive control. The negative control would help rule out false positive results whereas the positive control would help rule out false negative results. A specimen would be placed on a supporting surface such as, but not limited to, a membrane, ELISA well, gel, or other solid surface or placed in solution. Cells would be lysed with a lysing buffer and the DNA or RNA either immobilized on the support surface or solubilized in solution. Each specimen would be reacted in separate tests with one or more of the probes either simultaneously or sequentially in hybridization or other type tests. Detection of hybridization would be made through fluorescence analysis, bioluminescence, chemiluminescence, radioactivity counting, or other analyses. When employed in an ELISA-type assay, the development of color in solution or as a spot or through other type of standard analyses would be indicative of a positive reaction.

Positive reactivity with a probe specific for *E. coli* would identify the specimen as such. Such specimens would be unreactive with the *Shigella* probes. Similarly, one or more probes that elicit a positive response and are identifiers for *Shigella* would indicate the presence of *Shigella* in the specimen. Such specimens, if they contain only *Shigella*, should be unreactive with a probe specific for *E. coli*. One or more of the probes may react with one or more *Shigella* species, providing discrimination not only between *E. coli* and *Shigella*, but between one strain of *Shigella* and another. Thus, the probes may be capable of enhanced discrimination and may identify not only *Shigella* but a particular strain, such as *S. sonnei*.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Stock Cultures

The present example provides for the preparation of stock cultures for the studies provided herein. Strains of *Shigella sonnei* (ATCC 29930), *Shigella dysenteriae* (ATCC 13313), *Shigella boydii* (ATCC 8700), and *Shigella flexneri* (ATCC 29903) were obtained from the American Type Culture Collection (Rockville, Md.). *Escherichia coli* strains 0157:NM (CDC G5066) and 0157:H7 (CDC G5039) were provided by the Center for Disease Control (Atlanta, Ga.). For each of the four *Shigella* strains, lyophilized organisms were suspended in LB Broth and incubated in a shaker for several hours. A loopful of culture was removed and plated on LB agar overnight. Fresh isolated colonies were then incubated into LB broth and again grown overnight to prepare stock culture. Stocks were stored three different ways: on LB agar slants at room temperature, in LB broth containing 30% glycerol at −70° C., and in LB broth containing 30% glycerol in liquid nitrogen.

Example 2

Extraction of Genomic DNA

The present example provides methods used for extraction of genomic DNA from each of the four *Shigella* species. For extraction of genomic DNA, single colonies from the LB agar plate were grown in LB broth for several hours in a shaker incubator. This broth culture was then inoculated into a larger amount of LB broth in a 1-liter flask and shaken overnight at 35° C. Pellets of *Shigella* cells were collected by centrifugation and resuspended in buffer. Suspended pellets were transferred to sterile glass tubes, and sodium dodecyl sulfate and proteinase K were added to break open the cells. After adding salt and mixing thoroughly, prewarmed hexadecyltrimethylammonium bromide containing salt was mixed in. The mixture was briefly incubated in a water bath followed by the addition of chloroform:isoamyl alcohol for extraction.

The top, aqueous layer containing the nucleic acids was transferred to a fresh tube and the extraction steps repeated. To the final top, aqueous layer was added pure isopropanol, which resulted in the appearance of a stringy, white DNA pellet containing RNA that came out of solution and condensed into a tight mass. The nucleic acid was spooled up onto a glass rod, washed with 70% ethyl alcohol to remove residual chemicals, and dried under a vacuum/heater.

The dried nucleic acids were resuspended in buffer, RNase A was added, and the mixture incubated in a water bath to eliminate RNA contaminants. DNA in solution was then re-precipitated by adding very cold ethyl alcohol. Precipitated DNA was spooled using a glass rod and washed again with ethyl alcohol before being dried under a vacuum/heater. The dried DNA pellets were resuspended in buffer, the DNA concentration was determined, and each solution was diluted to a final concentration of 100 ng/μl.

Example 3

Amplification of the rDNA Gene by PCR

Amplifying the 16S ribosomal RNA gene involved the use of two primers having nucleotide sequences as shown by SEQ ID NOS: 1 and 2, buffer, magnesium chloride, deoxynucleotides, and the enzyme Taq polymerase. The primer sequences were based on literature reports for amplifying the 16S ribosomal RNA gene from *E. coli*. A separate reaction tube was used for each of the four *Shigella* species. The samples were then placed in a thermocycler, which used the following procedure in which the programs were linked, with 1 to 2 to 3 to 4:

| | |
|---|---|
| 95° C. for 6 minutes to denature double-stranded DNA | One cycle |
| 92° C. for 2 minutes to denature the DNA strands | Thirty cycles with next two steps |
| 42° C. for 45 seconds to anneal primers | |
| 72° C. for 4 minutes to extend the DNA chain | |
| 72° C. for 20 minutes to complete the extension | One cycle |
| 4° C. to hold the reaction mixture for further analysis | |

PCR products were run in agarose gels and fragment size was analyzed with a DNA ladder consisting of synthetic oligonucleotides of different sizes ranging from 100 base pairs to 22,000. For comparisons, *E. coli* strains that produce symptoms similar to *Shigella* were also tested in the PCR reaction after DNA had been isolated from them. Other species tested in the PCR reactions included *Bacillus subtilis* as well as different Vibrio species.

Example 4

Cloning the Amplification Product

The TA™ Cloning Kit from Invitrogen (San Diego, Calif.) was used together with the following strategy. The kit is designed for cloning PCR products directly from a PCR reaction without the need for modifying enzymes, purification, or digestions with restriction enzymes. The TA cloning vector, pCR™ II, contains the lacZa complementation fragment for blue-white color screening, ampicillin and kanamycin resistance genes for selection, and a versatile polylinker that contains EcoRi and Sp$^6$ and T7 priming sites. The amplified genomic material was ligated into the vector, using a ligation reaction for each *Shigella* species that included buffer, vector, PCR product, and T4 DNA ligase. The mixtures were incubated in a 12° C. water bath overnight. The expected result was to obtain a vector containing the genomic insert.

*E. coli* competent cells were then used to transform the vector containing the ligated DNA. The cells had a transformation efficiency of at least $1 \times 10^8$ transformants per microgram of supercoiled plasmid. For transforming the cells, LB agar plates were prepared with X-gal and ampicillin. The X-gal is a histochemical substrate for β-galactosidase and yields a blue precipitate on hydrolysis. Bacteria containing active β-galactosidase produce blue colonies when grown on media containing it. Cloning an insert into the pCR™ II plasmid disrupts the lacZa complementation fragment, preventing the production of active β-galactosidase.

The ligation reaction mixture was added to competent cells. Controls consisted of adding pUC18, a test plasmid. The cells were first kept on ice and briefly heat shocked to enhance plasmid uptake into the cells. After a further incubation, the cells were plated onto the prepared agar plates. The competent cell controls were plated onto plates devoid of ampicillin.

The pUC18 control showed an excellent reaction with thousands of blue colonies and less than 1% white. The plates with transformants for the 4 *Shigella* species showed mostly white colonies with about 5% blue colonies. The white transformants were picked and plated again on the X-gal-LB-ampicillin plates to check further for up to 48 hours of incubation at 35° C. The growth of all transformants on LB-kanamycin plates was also checked. All 40 transformants grew, showing the presence of plasmid PCR™ II, which confers resistance, in the transformants.

Example 5

Purifying the Cloned Plasmid DNA

Insta-Mini-Prep™ Kits obtained from 5 Prime-3 Prime, Inc. (Boulder, Colo.) were used to purify the cloned DNA from each of the four *Shigella* species. Transformed cells were grown in LB-ampicillin overnight. Plasmid DNA was extracted from each cell pellet with phenol-chloroform-isoamyl alcohol. The Insta-Mini-Prep column was added to the samples and then centrifuged. These steps were repeated several times until the last centrifugation left a top, clear aqueous phase containing the plasmid whereas the gel trapped unwanted contaminants. The recovered top phase was stored at 4° C. for analysis by PCR amplification and restriction digestion.

Example 6

Identifying the Cloned Segment

Three different tests were performed to verify that the correct genomic material from *Shigella* had been cloned. The first test consisted of digesting the plasmid miniprep with the restriction enzyme EcoRI and comparing the results on gels. Digestion reactions for each *Shigella* species included samples of the miniprep DNA, bovine serum albumin, and EcoRi enzyme obtained from Promega (Madison, Wis.). Samples were incubated in a water bath for 1 h, put on ice, and then analyzed with 0.8% agarose gels. The results showed patterns that were consistent with the presence of a 1,500 kb insert, the size expected based on the PCR reactions, in the plasmid. The results suggest that the 1,500-kb insert contains an EcoRI-restriction site that is cleaved to an 800 bp fragment and a 700 bp fragment by complete digestion with the restriction enzyme. The plasmid consists of 3.9 kb, which increases to 5.4 kb with the 1.5 kb insert.

The second set of tests focused on the use of primers rp1 and fD2, the same 16S ribosomal RNA primers as used previously to amplify the genomic DNA. The primers were used to specifically amplify the insert of 16S ribosomal RNA, if it were present in the plasmid. After amplification, the products were separated by gel electrophoresis to determine whether the band patterns were consistent with the size of the expected product. The gels showed that the primers had resulted in the amplification of a 1,500 bp fragment, as expected.

The third set of experiments depended on identifying PCR products that resulted from PCR amplification of minipreps using universal vector primers Sp6 and T7 (Invitrogen, San Diego, Calif.). The primers were added to a reaction mixture containing plasmid miniprep from each of the four *Shigella* species. The thermocycler program used was the same as in the previous PCR studies. The amplified products were then examined by using 0.8% agarose gels. Based on the known sequence of the plasmid, the products showed a 1,600-bp fragment, which includes the 1,500 bp-insert and part of the vector.

Example 7

Large-Scale Preparation of Plasmid DNA Containing the 16S Ribosomal RNA Gene Fragment The present example provides for large-scale preparation of plasmid DNA from transformed cells that contain the 16S ribosomal RNA gene fragments. Transformants were grown on LB-kanamycin plates at 35° C. overnight. A single colony from each growth was picked and then subcultured. The culture was then inoculated into a 1-liter flask and grown overnight. Cells were pelleted by centrifugation before being broken open with fresh lysozyme, sodium hydroxide, and sodium dodecyl sulfate. Potassium acetate and glacial acetic acid were added to the reaction mixture. After clarifying the solution by low-speed centrifugation, isopropanol was added, the mixture was re-centrifuged, and the precipitated DNA pellet was dried in a vacuum heater.

The extracted circular or closed plasmid DNA was further purified by high-speed centrifugation in cesium chloride. The procedures included the addition of cesium chloride and ethidium bromide followed by low-speed centrifugation to remove suspended particles. The clarified solution was poured into plastic centrifuge tubes, which were then sealed and balanced. The tubes were centrifuged at 60,000 rpm overnight at 20° C. The circular plasmid band was then collected under long-wave ultraviolet light by puncturing the tube with an 18-gauge needle. The plasmid DNA was then treated with sodium chloride-saturated isopropanol. The upper pink layer was discarded, and the process repeated until both layers remained colorless. The lower aqueous phase containing DNA was precipitated by standard procedures, treated with RNase, washed, dried, and resuspended in buffer for sequencing.

Example 8

Sequences of 16s rDNA Genes from *Shigella* Species

Sequencing reactions were carried out using Perkin Elmer Dye Terminator Cycle Sequencing Ready Reaction Kit Pat. No. 402079 with fluorescent terminators (Perkin Elmer, Foster City, Calif.). Single-stranded DNA template (0.5 µg) or double-stranded DNA template (0.2-0.5 µg), 0.8 pmol of primer for ss DNA or 3.2 pmol of primer for ds DNA, were combined in a final reaction volume of 20 µl. Standard manual sequencing procedures as recommended by Perkin Elmer were followed. The product was resuspended in loading buffer, boiled and loaded.

The 16s rDNA gene sequences are provided as SEQ ID NO:3 for *Shigella flexneri*, as SEQ ID NO:4 for *Shigella sonnei*, as SEQ ID NO:5 for *Shigella dysenteriae*, and as SEQ ID NO:6 for *Shigella boydii*. The first nucleotide of each sequence corresponds to nucleotide #8 of the *E. coli* sequence (SEQ ID NO:7). Therefore, to match a particular position in a *Shigella* sequence to the corresponding position in the reference *E. coli* sequence, the number seven is added to the position number of a *Shigella* nucleotide to match with the corresponding position of an "*E. coli* equivalent nucleotide".

Example 9

Genus-Specific and Species-Specific Nucleotides

The numbering of the nucleotides that are genus-specific or species-specific, as used herein and in Tables 2 and 3, result from aligning the obtained sequence with the sequence of the 16s rDNA gene from *E. coli* which is provided as SEQ ID NO:7, and assigning the corresponding number of the *E. coli* sequence to those bases that are different or that are missing in the *Shigella* sequence. Base insertions in the *Shigella* sequence are referred to as an "p" base, i.e., an insertion following base 88, for example, is referred to herein as base 88p so as to keep the numbering consistent with the *E. coli* numbering sequence. Alignment was done manually; probe sequences were analyzed against all known 16s RNA sequences of the Aligned Sequence Program, Ribosome Database Project, University of Illinois, Dept. of Microbiology, Urbana-Champaign, Ill., and against all sequences of Genbank, operated by the National Library of Medicine.

Table 2 provides sequence comparisons of 16s rDNA from *Shigella* species and *E. coli* species.

TABLE 2

Sequence comparisons of 16s rDNA from Shigella sp. and E. coli sp.

| ORGANISM | REGION[2] | SEQUENCE |
|---|---|---|
| | | 80　　　　　　　　90　　　　　　　　　　　100 |
| *E. coli* (ECORRD)[1]<br>SEQ ID NO: 8 | 71-100 | AACAGGAAGA　AGCTTGCTCT　　TT　　GCTGACGA |
| *E. coli* (rrnG)<br>(ECRRNGPK3)<br>SEQ ID NO: 23 | 71-100 | --------AC　--------G-　　-- /C\-------- |
| *E. coli* (rrrnE)<br>(ECRRNEPK3)<br>SEQ ID NO: 24 | 71-100 | ----------　--------/T\　　-- -- -------- |
| *E. coli* (rrnD)<br>(ECRNNDPK3)<br>SEQ ID NO: 23 | 71-100 | --------AC　--------G-　　-- /C\-------- |
| *E. coli* (rrnC)<br>(ECRRNCPK3)<br>SEQ ID NO: 25 | 71-4100 | --------AC　----------　　-- /C\-------- |
| *E. coli* (rrnB)<br>(ECRRNBPK3)<br>SEQ ID NO: 24 | 71-100 | ----------　--------/T\　　-- -- -------- |
| *E. coli*<br>ATCC 25922<br>SEQ ID NO: 26 | 71-100 | --------CG　--------/G\　　-- -- -------- |
| *E. coli* (rrnB)<br>(ECRRNBZ)<br>SEQ ID NO: 24 | 71-100 | ----------　--------/T\　　-- -- -------- |
| *E. coli*<br>ATCC 11775T<br>SEQ ID NO: 27 | 71-100 | ----------　--------/T\　　-- -- -------- |
| *E. coli* (rrnB)<br>(ECRRNBZ)<br>SEQ ID NO: 24 | 71-100 | ----------　--------/T\　　-- -- -------- |
| *E. coli* K-12<br>(ECOTSF)<br>SEQ ID NO: 24 | 71-100 | ----------　--------/T\　　-- -- -------- |
| *E. coli* (rrnB)<br>(ECORGNB)<br>SEQ ID NO: 24 | 71-100 | ----------　--------/T\　　-- -- -------- |
| *E. coli*<br>(ECOUW89)<br>SEQ ID NO: 24 | 71-100 | ----------　--------/T\　　-- -- -------- |
| *E. coli*<br>(ECOUW89)<br>SEQ ID NO: 24 | 71-100 | ----------　--------/T\　　-- -- -------- |
| *S. flexneri*<br>ATCC 12022<br>SEQ ID NO: 9 | 71-100 | --------C　--------G-　　-- /C\-------- |
| *S. flexneri*<br>French Strain<br>SEQ ID NO: 9 | 71-100 | --------C　--------G-　　-- /C\-------- |
| *S. flexneri*<br>ATCC 29903<br>(present<br>disclosure)<br>SEQ ID NO: 9 | 71-100 | --------C　--------G-　　-- /C\-------- |

TABLE 2-continued

Sequence comparisons of 16s rDNA from Shigella sp. and E. coli sp.

| ORGANISM | REGION[2] | SEQUENCE | | | |
|---|---|---|---|---|---|
| S. sonnei ATCC 9290 SEQ ID NO: 10 | 71-100 | --------AC | --------G- | -- /C\-------- | |
| S. sonnei French Strain SEQ ID NO: 10 | 71-100 | --------AC | --------G- | -- /C\-------- | |
| S. sonnei ATCC 29930 (present disclosure) SEQ ID NO: 10 | 71-100 | --------AC | --------G- | -- /C\-------- | |
| S. dysenteriae ATCC 13313 (present disclosure) SEQ ID NO: 11 | 71-100 | -----A---C | ---------- | -- -------- | |
| S. dysenteriae French Strain SEQ ID NO: 28 | 71-100 | ---------C | --------GC | -- /T\-------- | |
| S. dysenteriae ATCC 13313 SEQ ID NO: 29 | 71-100 | -----A---C | --------G- | -- -------- | |
| S. boydii ATCC 8700 (present disclosure) SEQ ID NO: 12 | 71-100 | ---------C | ---------- | -C -------- | |
| S. boydii ATCC 9207 SEQ ID NO: 9 | 71-100 | ---------C | --------G- | -- /C\-------- | |
| E. coli (ECORRD) SEQ ID NO: 13 | 961-991 | 970 CGATGCAACG | 980 CGAAGAACCT | 990 TACCTGGTCT | T |
| E. coli (rrrnG) (ECRRNGPK3) SEQ ID NO: 13 | 961-991 | ---------- | ---------- | ---------- | - |
| E. coli (rrrnE) (ECRRNEPK3) SEQ ID NO: 13 | 961-991 | ---------- | ---------- | ---------- | - |
| E. coli (rrrnD) (ECRRNDPK3) SEQ ID NO: 13 | 961-991 | ---------- | ---------- | ---------- | - |
| E. coli (rrnC) (ECRRNC) SEQ ID NO: 13 | 961-991 | ---------- | ---------- | ---------- | - |
| E. coli (rrnB) (ECRRNB) SEQ ID NO: 13 | 961-991 | ---------- | ---------- | ---------- | - |
| E. coli ATCC 25922 SEQ ID NO: 13 | 961-991 | ---------- | ---------- | ---------- | - |
| E. coli (rrnB) (ECRRNBZ) SEQ ID NO: 13 | 961-991 | ---------- | ---------- | ---------- | - |
| E. coli ATCC 11775T SEQ ID NO: 13 | 961-991 | ---------- | ---------- | ---------- | - |

TABLE 2-continued

Sequence comparisons of 16s rDNA from Shigella sp. and E. coli sp.

| ORGANISM | REGION[2] | SEQUENCE |
|---|---|---|
| E. coli (ECRRNBZ) SEQ ID NO: 13 | 961-991 | ---------- ---------- ---------- - |
| E. coli (ECOTSF) SEQ ID NO: 13 | 961-991 | ---------- ---------- ---------- - |
| E. coli (rrnB) (ECORGNB) SEQ ID NO: 13 | 961-991 | ---------- ---------- ---------- - |
| E. coli (ECOUW89) SEQ ID NO: 13 | 961-991 | ---------- ---------- ---------- - |
| E. coli (ECOUW89) SEQ ID NO: 13 | 961-991 | ---------- ---------- ---------- - |
| S. flexneri ATCC 12022 SEQ ID NO: 13 | 961-991 | ---------- ---------- ---------- - |
| S. flexneri French Strain SEQ ID NO: 13 | 961-991 | ---------- ---------- ---------- - |
| S. flexneri ATCC 29903 (present disclosure) SEQ ID NO: 13 | 961-991 | ---------- ---------- ---------- - |
| S. sonnei ATCC 29930 (present disclosure) SEQ ID NO: 14 | 961-991 | ---C------ -------X-- ---------- - |
| S. sonnei French Strain SEQ ID NO: 13 | 961-991 | ---------- ---------- ---------- - |
| S. sonnei ATCC 9290 SEQ ID NO: 13 | 961-991 | ---------- ---------- ---------- - |
| S. dysenteriae ATCC 13313 (present disclosure) SEQ ID NO: 13 | 961-991 | ---------- ---------- ---------- - |
| S. dysenteriae French Strain SEQ ID NO: 13 | 961-991 | ---------- ---------- ---------- - |
| S. dysenteriae ATCC 13313 SEQ ID NO: 13 | 961-991 | ---------- ---------- ---------- - |
| S. boydii ATCC 9207 SEQ ID NO: 13 | 961-991 | ---------- ---------- ---------- - |
| S. boydii ATCC 8700 (present disclosure) SEQ ID NO: 13 | 961-991 | ---------- ---------- ---------- - |

TABLE 2-continued

Sequence comparisons of 16s rDNA from Shigella sp. and E. coli sp.

| ORGANISM | REGION[2] | SEQUENCE | | | |
|---|---|---|---|---|---|
| E. coli (ECORRD) SEQ ID NO: 15 | 1001-1040 | 1010 GGAAGTTTTC 1040 GGGAACCGTG | 1020 AGAGATGAGA | ATG | 1030 TGCCTTC |
| E. coli (rrnD) (ECORRNDPK3) SEQ ID NO: 15 | 1001-1040 | ---------- ---------- | ---------- | --- | ------- |
| E. coli (rrnC) (ECORRNCPK3) SEQ ID NO: 30 | 1001-1040 | --------NN | ---------- | --- | ------- |
| E. coli (rrnC) (ECRRNBPK3) SEQ ID NO: 15 | 1001-1040 | ---------- ---------- | ---------- | --- | ------- |
| E. coli ATCC 25922 SEQ ID NO: 15 | 1001-1040 | ---------- ---------- | ---------- | --- | ------- |
| E. coli (ECRRNBZ) SEQ ID NO: 15 | 1001-1040 | ---------- ---------- | ---------- | --- | ------- |
| E. coli ATCC 11775T SEQ ID NO: 15 | 1001-1040 | ---------- ---------- | ---------- | --- | ------- |
| E. coli (rrnB) (ECRRNBZ) SEQ ID NO: 15 | 1001-1040 | ---------- ---------- | ---------- | --- | ------- |
| E. coli (ECOTSF) SEQ ID NO: 15 | 1001-1040 | A---C---C- ---------- | -------X-- | T-- | /G\------- |
| E. coli (rrnB) (ECORGNB) SEQ ID NO: 15 | 1001-1040 | ------T--- ---------- | ---------- | --- | ------- |
| E. coli (ECOUWB9) SEQ ID NO: 15 | 1001-1040 | ---------- ---------- | ---------- | --- | ------- |
| E. coli (ECOUW89) SEQ ID NO: 15 | 1001-1040 | ---------- ---------- | ---------- | --- | ------- |
| S. flexneri ATCC 12022 SEQ ID NO: 15 | 1001-1040 | ---------- ---------- | ---------- | --- | ------- |
| S. flexneri French Strain SEQ ID NO: 15 | 1001-1040 | ---------- ---------- | ---------- | --- | ------- |
| S. flexneri ATCC 29903 (present disclosure) SEQ ID NO: 15 | 1001-1040 | ---------- ---------- | ---------- | --- | ------- |
| S. sonnei ATCC 29930 (present disclosure) SEQ ID NO: 16 | 1001-1040 | A---C---C- ------T--- | -------X-- | T-- | /G\------ |

TABLE 2-continued

Sequence comparisons of 16s rDNA from Shigella sp. and E. coli sp.

| ORGANISM | REGION[2] | SEQUENCE | | | |
|---|---|---|---|---|---|
| S. sonnei<br>French Strain<br>SEQ ID NO: 32 | 1001-1040 | --------C- | -------GA- | -A- | /G\------- |
| S. sonnei<br>ATCC 9290<br>SEQ ID NO: 15 | 1001-1040 | ----------<br>---------- | ---------- | --- | ------- |
| S. dysenteriae<br>ATCC 13313<br>(present disclosure)<br>SEQ ID NO: 17 | 1001-1040 | A----C--C<br>-----T--- | -------X-- | /T\ | TG-------- |
| S. dysenteriae<br>French Strain<br>SEQ ID NO: 15 | 1001-1040 | ----------<br>---------- | ---------- | --- | ------- |
| S. dysenteriae<br>ATCC 13313<br>SEQ ID NO: 33 | 1001-1040<br>------T--- | A---CC--GT | ------AC-- | GG- | ------- -- |
| S. boydii<br>ATCC 9207<br>SEQ ID NO: 15 | 1001-1040 | ----------<br>---------- | ---------- | --- | ------- |
| S. boydii<br>ATCC 8700<br>(present disclosure)<br>SEQ ID NO: 15 | 1001-1040 | ----------<br>---------- | ---------- | --- | ------- |
| E. coli<br>(ECORRD)<br>SEQ ID NO: 34 | 245-280 | AGCTAGTAGG<br>GCGACG | TGGGGTAACG | GCTCACCTAG | |
| E. coli (rrnG)<br>(ECRRNGPK3)<br>SEQ ID NO: 34 | 245-280 | ----------<br>------ | ---------- | ---------- | |
| E. coli (rrnE)<br>(ECRRNEPK3)<br>SEQ ID NO: 34 | 245-280 | ----------<br>------ | ---------- | ---------- | |
| E. coli (rrnD)<br>(ECRRNDPK3)<br>SEQ ID NO: 35 | 245-280 | ----T--T--<br>------ | ---------- | -------A-- | |
| S. boydii<br>ATCC 8700<br>(present disclosure)<br>SEQ ID NO: 35 | 245-280 | ----T--T--<br>------ | ---------- | -------A-- | |

[1]Data for E. coli strain 7 are from the GenBank ECORRD Sequence Data Bank for 16s rDNA and are subject to Genbank descriptions. "X" as used herein means the absence of that nucleotide in comparison to the E. coli sequence. A dash "-" means the sequence is the same as that of E. coli. A symbol, "/ \" means an insertion of a nucleotide in a subsequent sequence as compared to that of E. coli ECORRD.
[2]The numbering of the region follows the numbering for the E. coli sequence ECORRD.

From Table 2 and the present disclosure, one of skill in the art would be able to determine nucleotides or combinations of nucleotides at particular positions that would distinguish *Shigella* from *E. coli* and among *Shigella* species. For example, identifying nucleotides for *Shigella sonnei* include a C at position 964, or a deletion at position 978; identifying nucleotides for *Shigella dysenteriae* includes an A at position 76; identifying nucleotides for *Shigella boydii* include a C at position 92; and identifying nucleotides for *E. coli* include a T at position 88p.

Table 3 provides a listing of exemplary genus-specific and species-specific probe molecules having select species-specific or genus-specific nucleotides distinguishing *Shigella* from *E. coli*, distinguishing *E. coli* from *Shigella* species, and identifying *S. sonnei*.

Specificity of hybridization is dependent upon probe length, about 15 bases being average for bacterial genomes. Shorter probe sequences may be used, as well as longer sequences; however, the effect of a one base mismatch is decreased with a longer probe.

One of skill in this art would realize in light of the present disclosure that a probe nucleic acid molecule designed to detect a base match or mismatch at a certain nucleotide position would optimally be positioned near the middle of the molecule, i.e., there would be about as many nucleotides 5' to the matched or mismatched site as are 3' to said site. Flexibility exists, however, especially since GC base pairs hydrogen bond more strongly than AT base pairs. An AT rich half of a candidate probe molecule in relation to said site may need to be made longer to account for the lower strength of binding.

TABLE 3

Exemplary Genus-Specific and Species-Specific Probe Molecules

| Basis for Probe Selection | Probe Sequence (20 mer) | |
|---|---|---|
| *S. boydii* (80-100) | C AGCTTGCTCT TCGCTGACG[1], SEQ ID NO: 18 | *E. coli* sequence shows a different set of nucleotides at underlined positions as seen in Table 2. |
| *S. dysenteriae* (76-94) | AAAGC AGCTTGCTCT TTGCT, SEQ ID NO: 19 | *E. coli* sequence shows a different nucleotide at underlined positions as seen in Table 2. |
| *S. sonnei* (961-980) | CGACGCAACG CGAAGAAXCT T[2], SEQ ID NO: 20 | Based on the data of Table 2, this sequence appears unique to *S. sonnei*. |
| *E. coli* (79-98) | GA AGCTTGCT/T\CT TTGCTGAC[3], SEQ ID NO: 21 | Presence of T at 88p identifies *E. coli*. Shigella sequences differ. A few nucleotides toward the 3' end, the insertion of a C in the Shigella sequence causes the sequence to realign correctly with the *E. coli* sequence. |

[1]Bases underlined indicate a change in sequence relative to *E. coli* (ECORRD)
[2]X indicates the deletion of a base relative to the *E. coli* (ECORRD) sequence
[3]The symbol /T\ indicates a base insertion, in this case, insertion of T One of skill in the art in light of this disclosure would be able to identify further combinations of nucleotides that would uniquely identify a particular strain of *Shigella* described herein by comparing nucleotides at particular positions. Such combinations are considered to be part of the present disclosure.

Example 10

Design of Probes for Identifying *Shigella* sp

Nucleic acid probes are designed for discriminatory hybridization to 16s rRNA or 16s rDNA from test samples for the identification of *Shigella* sp. based upon information provided herein and knowledge of the melting temperatures of probe sequences. The melting temperature of a DNA probe of less than about 40 bases can be calculated by the formula:

(#purines×4 degrees)+(#pyrimidines×2 degrees)=$Tm$.

Thus, high GC containing probes have a higher melting temperature than probes having a high AT content. The general ability to discriminate between templates having a one base mismatch has been known in the field of nucleic acid hybridization for years.

One of skill in this art in light of the present disclosure would also realize that a set of two or more probes (nucleic acid molecules) may be used to distinguish/identify a species or genus of bacteria. A first probe of a set may eliminate certain species/genera while a second probe of a set may eliminate further species/genera so as to provide identifications in combination with the results from using the first probe.

Each nucleic acid probe is tested to demonstrate adequate exclusivity as to all other organisms, adequate inclusivity with respect to *Shigella* sp., accessibility of the target regions under various assay conditions that may be employed in test circumstances, and intramolecular interactions of the probe itself.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References cited herein, to the extent that they provide exemplary procedural or other details supplementary to those set forth herein, are specifically incorporated herein by reference.

What is claimed is:

1. An isolated nucleic acid molecule consisting of
SEQ ID NO 3, SEQ ID NO. 4, SEQ ID NO: 5, or SEQ ID NO: 6,
or an RNA equivalent thereof,
or a nucleic acid complementary to said isolated molecule, capable of base-pairing according to the standard Watson-Crick complementarity rules,
or a nucleic acid substantially complementary to said isolated molecule which is capable of hybridizing to the nucleic acid molecule under the following stringent conditions:
hybridization at 40°-65° C. for 14-16 hours in a hybridization solution at ph 7.8, containing 0.9 M NaCl, 0.12 M Tris-HCl, 6 nM EDTA, 0.1M sodium phosphate buffer, 0.1% SDS and 0.1% polyvinylpyrrolidone,
followed by three 15-minute washes at 40°-65° C. to remove unbound probes in a solution at pH 7, containing 0.075 M NaCl, 0.0075 M Na Citrate and 0.1% SDS.

2. The isolated nucleic acid molecule consisting of the nucleotide sequence of SEQ ID NO: 6.

3. An isolated nucleic acid molecule comprising a nucleotide sequence of SEQ ID NO: 3, SEQ ID NO: 4, SEQ ID NO: 5, or SEQ ID NO: 6,
or an RNA equivalent thereof,
or a nucleic acid complementary to said isolated molecule, capable of base-pairing according to the standard Watson-Crick complementarity rules.

4. A probe which
a) targets *Shigella flexneri* comprising a fragment greater than 10 to 40 bases in length of a nucleotide sequence SEQ ID NO: 3, an RNA equivalent thereof, or a nucleic acid complementary to said molecule, capable of base-pairing according to the standard Watson-Crick complementarity rules,
b) targets *Shigella sonnei* comprising a fragment greater than 10 to 40 bases in length of a nucleotide sequence SEQ ID NO: 4, an RNA equivalent thereof, or a nucleic acid complement try to said molecule, capable of base-pairing according to the standard Watson-Crick complementarity rules,
c) targets *Shigella dysenteriae* comprising a fragment greater than 10 to 40 bases in length of a nucleotide sequence SEQ ID NO: 5, an RNA equivalent thereof, or a nucleic acid complementary to said molecule, capable of base-pairing according to the standard Watson-Crick complementarity rules,
or
d) targets *Shigella boydii* comprising a fragment greater than 10 to 40 bases in length of a nucleotide sequence SEQ ID NO: 6, an RNA equivalent thereof, or a nucleic acid complement try to said molecule, capable of base-pairing according to the standard Watson-Crick complementarity rules.

5. A probe which
a) targets *Shigella flexneri* consisting of a fragment greater than 10 to 40 bases in length of a nucleotide sequence SEQ ID NO: 3, an RNA equivalent thereof, or a nucleic acid complement try to said molecule, capable of base-pairing according to the standard Watson-Crick complementarity rules,
b) targets *Shigella sonnei* consisting of a fragment greater than 10 to 40 bases in length of a nucleotide sequence SEQ ED NO: 4, an RNA equivalent thereof, or a nucleic acid complementary to said molecule, capable of base-pairing according to the standard Watson-Crick complementarity rules,
c) targets *Shigella dysenteriae* consisting of a fragment greater than 10 to 40 bases in length of a nucleotide sequence SEQ ID NO: 5, an RNA equivalent thereof, or a nucleic acid complementary to said molecule, capable of base-pairing according to the standard Watson-Crick complementarity rules,
or
d) targets *Shigella boydii* consisting of a fragment greater than 10 to 40 bases in length of a nucleotide sequence SEQ ID NO: 6, an RNA equivalent thereof, or a nucleic acid complementary to said molecule, capable of base-pairing according to the standard Watson-Crick complementarity rules.

6. A probe as in claim 4 which comprises 15-25 bases in length.

7. A probe as in claim 5 which comprises 15-25 bases in length.

* * * * *

```
                              SEQUENCE LISTING

<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Nucleotide
      sequence of a forward primer for amplifying 16s
      rDNA gene by PCR

<400> SEQUENCE: 1
agagtttgat catggctcag                                                   20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Nucleotide
      sequence of a reverse primer for amplifying 16s
      rDNA gene by PCR

<400> SEQUENCE: 2
acggttacct tgttacgact t                                                 21

<210> SEQ ID NO 3
<211> LENGTH: 1506
<212> TYPE: DNA
<213> ORGANISM: Shigella flexneri

<400> SEQUENCE: 3
agagtttgat catggctcag attgaacgct ggcggcaggc ctaacacatg caagtcgaac        60
ggtaacagga agcagcttgc tgtttcgctg acgagtggcg gacgggtgag taatgtctgg       120
gaaactgcct gatggagggg gataactact ggaaacggta gctaataccg cataacgtcg       180
caagaccaaa gagggggacc ttcgggcctc ttgccatcgg atgtgcccag atgggattag       240
ctagtaggtg gggtaacggc tcacctaggc gacgatccct agctggtctg agaggatgac       300
cagccacact ggaactgaga cacggtccag actcctacgg gaggcagcag tggggaatat       360
tgcacaatgg gcgcaagcct gatgcagcca tgccgcgtgt atgaagaagg ccttcgggtt       420
gtaaagtact ttcagcgggg aggaagggag taaagttaat cctttgctc attgacgtta       480 cccgcagaag aagcaccggc taactccgtg ccagcagccg cggtaatacg gagggtgcaa       540
gcgttaatcg gaattactgg gcgtaaagcg cacgcaggcg gtttgttaag tcagatgtga       600
aatccccggg ctcaacctgg gaactgcatc tgatactggc aagcttgagt ctcgtagagg       660
ggggtagaat tccaggtgta gcggtgaaat gcgtaaagat ctggaggaat accggtggcg       720
aaggcggccc cctggacgaa gactgacgct caggtgcgaa agcgtgggga gcaaacagga       780
ttagataccc tggtagtcca cgctgtaaac gatgtcgact tggaggttgt gcccttgagg       840
tgtggcttcc ggagctaacg cgttaagtcg accgcctggg gagtacggcc gcaaggttaa       900
aactcaaatg aattgacggg ggcccgcaca agcggtggag catgtggttt aattcgatgc       960
aacgcgaaga accttacctg gtcttgacat ccacggaagt tttcagagat gagaatgtgc      1020
```

```
cttcgggaac cgtgagacag gtgctgcatg gctgtcgtca gctcgtgttg tgaaatgttg    1080
ggttaagtcc cgcaacgagc gcaacccttta tcctttgttg ccagcggtcc ggccgggaac    1140
tcaaaggaga ctgccagtga taaactggag gaaggtgggg atgacgtcaa gtcatcatgg    1200
cccttacgac cagggctaca cacgtgctac aatggcgcat acaaagagaa gcgacctcgc    1260
gagagcaagc ggacctcata aagtgcgtcg tagtccggat tggagtctgc aactcgactc    1320
catgaagtcg gaatcgctag taatcgtgga tcagaatgcc acggtgaata cgttcccggg    1380
ccttgtacac accgcccgtc acaccatggg agtgggttgc aaaagaagta ggtagcttaa    1440
ccttcgggag ggcgcttacc actttgtgat tcatgactgg ggtgaagtcg taacaaggta    1500
accgta                                                               1506
```

<210> SEQ ID NO 4
<211> LENGTH: 1505
<212> TYPE: DNA
<213> ORGANISM: Shigella sonnei

<400> SEQUENCE: 4

```
agagtttgat catggctcag attgaacgct ggcggcaggc ctaacacatg caagtcgaac      60
ggtaacagga aacagcttgc tgtttcgctg acgagtggcg gacgggtgag taatgtctgg    120
gaaactgcct gatggagggg gataaactact ggaaacggta gctaataccg cataacgtcg    180
caagaccaaa gagggggacc ttcgggcctc ttgccatcgg atgtgcccag atgggattag    240
ctagtaggtg gggtaacggc tcacctaggc gacgatccct agctggtctg agaggatgac    300
cagccacact ggaactgaga cacggtccag actcctacgg gaggcagcag tggggaatat    360
tgcacaatgg gcgcaagcct gatgcagcca tgccgcgtgt atgaagaagg cttcgggtt    420 gtaaagtact ttcagcgggg aggaagggag taaagttaat acctttactc attgacgtta    480
cccgcagaag aagcaccggc taactccgtg ccagcagccg cggtaatacg gagggtgcaa    540
gcgttaatcg gaattactgg gcgtaaagcg cacgcaggcg gtttgttaag tcagatgtga    600
aatccccggg ctcaacctgg gaactgcatc tgatactggc aagcttgagt ctcgtagagg    660
ggggtagaat tccaggtgta gcggtgaaat gcgtagagat ctggaggaat accggtggcg    720
aaggcggccc cctggacgaa gactgacgct caggtgcgaa agcgtgggga gcaaacagga    780
ttagataccc tggtagtcca cgccgtaaac gatgtcgact tggaggttgt gcccttgagg    840
cgtggcttcc ggagctaacg cgttaagtcg accgcctggg gagtacggcc gcaaggttaa    900
aactcaaatg aattgacggg ggcccgcaca agcggtggag catgtggttt aattcgacgc    960
aacgcgaaga acttacctgg tcttgacatc cacggaactt tccagagatg gattggtgcc   1020
ttcgggaact gtgagacagg tgctgcatgg ctgtcgtcag ctcgtgttgt gaaatgttgg   1080
gttaagtccc gcaacgagcg caacccttat cctttgttgc cagcggtccg gccgggaact   1140
caaaggagac tgccagtgat aaactggagg aaggtgggga tgacgtcaag tcatcatggc   1200
ccttacgacc agggctacac acgtgctaca atggcgcata caaagagaag cgacctcgcg   1260
agagcaagcg gacctcataa agtgcgtcgt agtccggatt ggagtctgca actcgactcc   1320
atgaagtcgg aatcgctagt aatcgtggat cagaatgcca cggtgaatac gttcccgggc   1380
cttgtacaca ccgcccgtca caccatggga gtgggttgca aaagaagtag gtagcttaac   1440 cttcggagg gcgcttacca ctttgtgatt catgactggg gtgaagtcgt aacaaggtaa   1500
ccgta                                                              1505
```

```
<210> SEQ ID NO 5
<211> LENGTH: 1453
<212> TYPE: DNA
<213> ORGANISM: Shigella dysenteriae
<220> FEATURE:
<221> NAME/KEY: modified_base
<222> LOCATION: (400)..(998)
<223> OTHER INFORMATION: N = Unknown

<400> SEQUENCE: 5
agagtttgat catggctcag attgaacgct ggcggcaggc ctaacacatg caagtcgaac    60
ggtaacagaa agcagcttgc tcctttgctg acgagtggcg gacgggtgag taatgtctgg   120
gaaactgcct gatggagggg gataactact ggaaacggta gctaataccg cataacgtcg   180
caagaccaaa gaggggggacc ttcgggcctc ttgccatcgg atgtgcccag atgggattag   240
ctagtagtgg ggtaacggct cacctaggcg acgatcccta gctggtctga gaggatgacc   300
agccacactg gaactgagac acggtccaga ctcctacggg aggcagcagt ggggaatatt   360
gcacaatggg cgcaagcctg atgcagccat gccgcgtgtn tgaanaaggc cttcggttg    420
taaagtactt tcagcgggga ggaagggagt aaagttaata cctttgctca ttgacgttac   480
ccgcagaaga agcaccggct aactccgtgc cagcagccgc ggtaatacgg agggtgcaag   540
cgttaatcgg aattactggg cgtaaagcgc acgcaggcg tttgttaaat canatgtgaa    600
atccccgggc tcaacctggg aactgcatct gatactggca ancttgagtc tcgtagaggg   660
gggtagaatt ccaggtgtag cggtgaaatg cgtagagatc tggaggaata ccggtggcga   720
aggcggcccc ctggacnaag actgacgctc aggtgcgaaa gcgtgggag caaacaggat    780
tagatacct ggtagtccac gccgtaaacg atgtcgactt ggaggttgtg cccttgaggc    840
gtggcttccg gagctaacgc gttaagtcga ccgcctgggg agtacggccg caaggttaaa   900
actcaaatga attgacgggg gcccgcacaa gcggtggagc atgtggttta attcgatgca   960
acgcgaanaa ccttacctgg tcttgacatc cacagaanct tccagagatg gattggtgcc  1020
ttcgggaact gtgagacagg tgctgcatgg ctgtcgtcag ctcgtgttgt gaaatgttgg  1080
gttaagtccc gcaacgagcg caacccttat cctttgttgc cagcggtccg gccgggaact  1140
caaaggagac tgccagtgat aaactggagg aaggtgggga tgacgtcaag tcatcatggc  1200
ccttacgacc agggctacac acgtgctaca atggcgcata aaagagaag cgacctcgcg   1260
agagcaagcg gacctcataa agtgcgtcgt agtccggatt ggagtctgca actcgactcc  1320
atgaagtcgg aatcgctagt aatcgtggat cagaatgtca cggtgaatac gttcccgggc  1380
cttgtacaca ccgcccgtca caccatggga gtggcttaac cttcgggagg gcgcttacca  1440
ctttgtgatt cat                                                    1453

<210> SEQ ID NO 6
<211> LENGTH: 1505
<212> TYPE: DNA
<213> ORGANISM: Shigella boydii

<400> SEQUENCE: 6
agagtttgat catggctcag attgaacgct ggcggcaggc ctaacacatg caagtcgaac    60
ggtaacagga agcagcttgc tcttcgctga cgagtggcgg acgggtgagt aatgtctggg   120
aaactgcctg atggaggggg ataactactg gaaacggtag ctaataccgc ataatgtcgc   180
aagaccaaag aggggggacct tcgggcctct tgccatcgga tgtgcccaga tgggattagc   240
ttgttggtgg ggtaacggct caccaaggcg acgatcccta gctggtctga gaggatgacc   300
```

| | |
|---|---:|
| agccacatgg aactgagaca cggtccagac tcctacggga ggcagcagtg gggaatattg | 360 |
| cacaatgggc gcaagcctga tgcagccatg ccgcgtgtat gaagaaggcc ttcgggttgt | 420 |
| aaagtacttt cagcggggag gaagggagta aagttaatac ctttgctcat tgacgttacc | 480 |
| cgcagaagaa gcaccggcta actccgtgcc agcagccgcg gtaatacgga gggtgcaagc | 540 |
| gttaatcgga attactgggc gtaaagcgca cgcaggcggt ttgttaagtc agatgtgaaa | 600 |
| tccccgggct caacctggga actgcatctg atactggcaa gcttgagtct cgtagagggg | 660 |
| ggtagaattc caggtgtagc ggtgaaatgc gtagagatct ggaggaatac cggtggcgaa | 720 |
| ggcggccccc tggacgaaga ctgacgctca ggtgcgaaag cgtgggagc aaacaggatt | 780 |
| agataccctg gtagtccacg ccgtaaacga tgtcgacttg gaggttgtgc ccttgaggcg | 840 |
| tggcttccgg agctaacgcg ttaagtcgac cgcctgggga gtacggccgc aaggttaaaa | 900 |
| ctcaaatgaa ttgacggggg cccgcacaag cggtggagca tgtggtttaa ttcgatgcaa | 960 |
| cgcgaagaac cttacctggt cttgacatcc acggaagttt tcagagatga gaatgtgcct | 1020 |
| tcggaaccg tgagacaggt gctgcatggc tgtcgtcagc tcgtgttgtg aaatgttggg | 1080 |
| ttaagtcccg caacgagcgc aacccttatc ctttgttgcc agcggtccgg ccgggaactc | 1140 |
| aaaggagact gccagtgata aactggagga aggtggggat gacgtcaagt catcatggcc | 1200 |
| cttacgacca gggctacaca cgtgctacaa tggcgcatac aaagagaagc gacctcgcga | 1260 |
| gagcaagcgg acctcataaa gtgcgtccgt agtccggatt ggagtctgca actcgactcc | 1320 |
| atgaagtcgg aatcgctagt aatcgtggat cagaatgcca cggtgaatac gttcccgggc | 1380 |
| cttgcacaca ccgcccgtca caccatggga gtgggttgca aaagaagtag gtagcttaac | 1440 |
| cttcgggagg cgcttacca ctttgtgatt catgactggg gtgaagtcgt aacaaggtaa | 1500 |
| ccgta | 1505 |

<210> SEQ ID NO 7
<211> LENGTH: 1541
<212> TYPE: DNA
<213> ORGANISM: Escherichia coli

<400> SEQUENCE: 7

| | |
|---|---:|
| aaattgaaga gtttgatcat ggctcagatt gaacgctggc ggcaggccta acacatgcaa | 60 |
| gtcgaacggt aacaggaaga agcttgctct ttgctgacga gtggcggacg ggtgagtaat | 120 |
| gtctgggaaa ctgcctgatg gagggggata actactggaa acggtagcta ataccgcata | 180 |
| acgtcgcaag accaaagagg gggaccttcg ggcctcttgc catcggatgt gcccagatgg | 240 |
| gattagctag taggtggggt aacggctcac ctaggcgacg atccctagct ggtctgagag | 300 |
| gatgaccagc cacactggaa ctgagacacg gtccagactc ctacgggagg cagcagtggg | 360 |
| gaatattgca caatgggcgc aagcctgatg cagccatgcc gcgtgtatga agaaggcctt | 420 |
| cgggttgtaa agtactttca gcggggagga agggagtaaa gttaatacct tgctcattg | 480 |
| acgttacccg cagaagaagc accggctaac tccgtgccag cagccgcggt aatacggagg | 540 |
| gtgcaagcgt taatcggaat tactgggcgt aaagcgcacg caggcggttt gttaagtcag | 600 |
| atgtgaaatc cccgggctca acctgggaac tgcatctgat actggcaagc ttgagtctcg | 660 |
| tagaggggg tagaattcca ggtgtagcgg tgaaatgcgt agagatctgg aggaataccg | 720 |
| gtggcgaagg cggccccctg gacgaagact gacgctcagg tgcgaaagcg tgggagcaa | 780 |
| acaggattag ataccctggt agtccacgcc gtaaacgatg tcgacttgga ggttgtgccc | 840 |

```
ttgaggcgtg gcttccggag ctaacgcgtt aagtcgaccg cctggggagt acggccgcaa    900
ggttaaaact caaatgaatt gacggggggcc cgcacaagcg gtggagcatg tggtttaatt    960
cgatgcaacg cgaagaacct tacctggtct tgacatccac ggaagttttc agagatgaga   1020
atgtgccttc gggaaccgtg agacaggtgc tgcatggctg tcgtcagctc gtgttgtgaa   1080
atgttgggtt aagtcccgca acgagcgcaa cccttatcct ttgttgccag cggtccggcc   1140
gggaactcaa aggagactgc cagtgataaa ctggaggaag gtgggggatga cgtcaagtca   1200 tcatggccct tacgaccagg gctacacacg tgctacaatg gcgcatacaa agagaagcga   1260
cctcgcgaga gcaagcggac ctcataaagt gcgtcgtagt ccggattgga gtctgcaact   1320
cgactccatg aagtcggaat cgctagtaat cgtggatcag aatgccacgg tgaatacgtt   1380
cccgggcctt gtacacaccg cccgtcacac catgggagtg ggttgcaaaa gaagtaggta   1440
gcttaacctt cgggagggcg cttaccactt tgtgattcat gactggggtg aagtcgtaac   1500
aaggtaaccg tagggaacc tgcggttgga tcacctcctt a                          1541

<210> SEQ ID NO 8
<211> LENGTH: 30
<212> TYPE: DNA
<213> ORGANISM: Escherichia coli

<400> SEQUENCE: 8
aacaggaaga agcttgctct tgctgacga                                           30

<210> SEQ ID NO 9
<211> LENGTH: 31
<212> TYPE: DNA
<213> ORGANISM: Shigella flexneri

<400> SEQUENCE: 9
aacaggaagc agcttgctgt ttcgctgacg a                                        31

<210> SEQ ID NO 10
<211> LENGTH: 31
<212> TYPE: DNA
<213> ORGANISM: Shigella sonnei

<400> SEQUENCE: 10
aacaggaaac agcttgctgt ttcgctgacg a                                        31

<210> SEQ ID NO 11
<211> LENGTH: 30
<212> TYPE: DNA
<213> ORGANISM: Shigella dysenteriae

<400> SEQUENCE: 11
aacagaaagc agcttgctct ttgctgacga                                          30

<210> SEQ ID NO 12
<211> LENGTH: 30
<212> TYPE: DNA
<213> ORGANISM: Shigella boydii

<400> SEQUENCE: 12
aacaggaagc agcttgctct tcgctgacga                                          30

<210> SEQ ID NO 13
<211> LENGTH: 31
<212> TYPE: DNA
<213> ORGANISM: Escherichia coli
```

<400> SEQUENCE: 13
cgatgcaacg cgaagaacct tacctggtct t                          31

<210> SEQ ID NO 14
<211> LENGTH: 30
<212> TYPE: DNA
<213> ORGANISM: Shigella sonnei

<400> SEQUENCE: 14
cgacgcaacg cgaagaactt acctggtctt                            30

<210> SEQ ID NO 15
<211> LENGTH: 40
<212> TYPE: DNA
<213> ORGANISM: Escherichia coli

<400> SEQUENCE: 15
ggaagttttc agagatgaga atgtgccttc gggaaccgtg                  40

<210> SEQ ID NO 16
<211> LENGTH: 40
<212> TYPE: DNA
<213> ORGANISM: Shigella sonnei

<400> SEQUENCE: 16
agaactttcc agagatggat tggtgccttc gggaactgtg                  40

<210> SEQ ID NO 17
<211> LENGTH: 40
<212> TYPE: DNA
<213> ORGANISM: Shigella dysenteriae

<400> SEQUENCE: 17
agaagcttcc agagatggat tggtgccttc gggaactgtg                  40

<210> SEQ ID NO 18
<211> LENGTH: 20
<212> TYPE: DNA
<213> ORGANISM: Shigella boydii

<400> SEQUENCE: 18
cagcttgctc ttcgctgacg                                       20

<210> SEQ ID NO 19
<211> LENGTH: 20
<212> TYPE: DNA
<213> ORGANISM: Shigella dysenteriae

<400> SEQUENCE: 19
aaagcagctt gctctttgct                                       20

<210> SEQ ID NO 20
<211> LENGTH: 20
<212> TYPE: DNA
<213> ORGANISM: Shigella sonnei

<400> SEQUENCE: 20
cgacgcaacg cgaagaactt                                       20

<210> SEQ ID NO 21
<211> LENGTH: 21
<212> TYPE: DNA

<213> ORGANISM: Escherichia coli

<400> SEQUENCE: 21
gaagcttgct tctttgctga c          21

<210> SEQ ID NO 22
<211> LENGTH: 17
<212> TYPE: DNA
<213> ORGANISM: Shigella sonnei

<400> SEQUENCE: 22
cgacgcaacg cgaagaa          17

<210> SEQ ID NO 23
<211> LENGTH: 31
<212> TYPE: DNA
<213> ORGANISM: Escherichia coli

<400> SEQUENCE: 23
aacaggaaac agcttgctgt ttcgctgacg a          31

<210> SEQ ID NO 24
<211> LENGTH: 31
<212> TYPE: DNA
<213> ORGANISM: Escherichia coli

<400> SEQUENCE: 24
aacaggaaga agcttgcttc tttgctgacg a          31

<210> SEQ ID NO 25
<211> LENGTH: 31
<212> TYPE: DNA
<213> ORGANISM: Escherichia coli

<400> SEQUENCE: 25
aacaggaaac agcttgctct ttcgctgacg a          31

<210> SEQ ID NO 26
<211> LENGTH: 31
<212> TYPE: DNA
<213> ORGANISM: Escherichia coli

<400> SEQUENCE: 26
aacaggaacg agcttgctgc tttgctgacg a          31

<210> SEQ ID NO 27
<211> LENGTH: 31
<212> TYPE: DNA
<213> ORGANISM: Escherichia coli

<400> SEQUENCE: 27
aacaggaagc agcttgctgc tttgctgacg a          31

<210> SEQ ID NO 28
<211> LENGTH: 31
<212> TYPE: DNA
<213> ORGANISM: Shigella dysenteriae

<400> SEQUENCE: 28
aacaggaagc agcttgctgc tttgctgacg a          31

<210> SEQ ID NO 29
<211> LENGTH: 30

<212> TYPE: DNA
<213> ORGANISM: Shigella dysenteriae

<400> SEQUENCE: 29
aacagaaagc agcttgctgt ttgctgacga                                         30

<210> SEQ ID NO 30
<211> LENGTH: 40
<212> TYPE: DNA
<213> ORGANISM: Escherichia coli
<220> FEATURE:
<221> NAME/KEY: modified_base
<222> LOCATION: (9)..(10)
<223> OTHER INFORMATION: N = Unknown

<400> SEQUENCE: 30
ggaagtttnn agagatgaga atgtgccttc gggaaccgtg                              40

<210> SEQ ID NO 31
<211> LENGTH: 40
<212> TYPE: DNA
<213> ORGANISM: Escherichia coli

<400> SEQUENCE: 31
agaactttcc agagatggat tggtgccttc gggaactgtg                              40

<210> SEQ ID NO 32
<211> LENGTH: 41
<212> TYPE: DNA
<213> ORGANISM: Shigella sonnei

<400> SEQUENCE: 32
ggaagtttcc agagatggaa aaggtgcctt cgggaaccgt g                            41

<210> SEQ ID NO 33
<211> LENGTH: 40
<212> TYPE: DNA
<213> ORGANISM: Shigella dysenteriae

<400> SEQUENCE: 33
agaaccttgt agagatacga gggtgccttc gggaactgtg                              40

<210> SEQ ID NO 34
<211> LENGTH: 36
<212> TYPE: DNA
<213> ORGANISM: Escherichia coli

<400> SEQUENCE: 34
agctagtagg tggggtaacg gctcacctag gcgacg                                  36

<210> SEQ ID NO 35
<211> LENGTH: 36
<212> TYPE: DNA
<213> ORGANISM: Escherichia coli

<400> SEQUENCE: 35
agcttgttgg tggggtaacg gctcaccaag gcgacg                                  36